United States Patent [19]

Holtkamp

[11] Patent Number: Plant 5,602

[45] Date of Patent: Dec. 17, 1985

[54] AFRICAN VIOLET PLANT NAMED IMPROVED LOUISIANA

[75] Inventor: Reinhold Holtkamp, Isselburg, Fed. Rep. of Germany

[73] Assignee: Gessellschaftsvertrag uber die Ergindergemeinschaft "OPTIMARA", Rees Haffen, Fed. Rep. of Germany

[21] Appl. No.: 568,442

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Improved Louisiana characterized by its compact habit, strong and upright flower stems, frilled flowers which are light pink accentuated with darker pink spots around the center and in certain instances darker pink at the edges, and by its dark green and indented leaves.

1 Drawing Figure

The present invention comprises a new and distinct cultivar of African violet plant, botanically known as *Saintpaulia ionantha,* and named Improved Louisiana.

The new cultivar was referred to during the breeding and selection process by the designation G 9/VIII, and is a product of a planned breeding program. The basic objective of the breeding program was to create an African violet cultivar improving in certain respects the characteristics of the cultivar Louisiana, disclosed in my U.S. Plant Pat. No. 4,348.

The new cultivar was originated from a cross made in a controlled breeding program in Isselburg, West Germany. The female, or seed parent was a cultivar designated d 150/2 red girl. The male, or pollen parent was a cultivar designated d 134/11 lilac frilled.

The new cultivar Improved Louisiana was discovered and selected by me as a flowering plant within the progeny of the stated cross in a controlled environment in Isselburg, West Germany, Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Improved Louisiana has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Improved Louisiana, which in comination distinguish this African violet as a new and distinct cultivar:

1. The flower color is light pink with dark pink spots at the center of the flower.
2. Compact growth habit.
3. The flowers are frilled at the edges.
4. The flower stems are upright and strong and relatively abundant, thereby producing a tight flower bouquet well above the leaves.

5. The leaf petioles do not stretch when grown close together, thereby increasing productivity.

The new cultivar is most similar to the cultivar Louisiana, referred to above, and was developed to improve certain characteristics of Louisiana. In comparison to Louisiana, the new cultivar has a somewhat darker pink flower color, the flowers have frilled edges and are somewhat more round, has a more compact growth habit, and the leaves are darker and indented at the edges.

The accompany photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 3:00 P.M. in late November in Nashville, Tenn.

Botanical classification: *Saintpaulia ionantha,* Ramat. cv. IMPROVED LOUISIANA.

Parentage:

*Male parent.*—d 134/11 lilac frilled.

*Female parent.*—d 150/2 red girl.

Propagation: The new cultivar holds its distinguishing characteristics through successive propagations by leaf cuttings and by division of shoots.

Plant: From 5 cm. to 7 cm. tall when grown in pots, and approximately 22–25 cm. in diameter when fully grown.

*Leaves.*—General Form: Oval to heart shape. Diameter: 60–65 mm. Texture: Leather-like. Aspect: Slightly hairy; medium green. Veins: Pronounced light green from underside. Color (upperside): Yellow green 147A. Color (underside): Yellow green 147D. Petiole: Short, strong, brownish green.

*Flowers.*—Buds: Ball shape. Sepals: 5, spear shape. Color: Dark brown. Calyx: Flat funnel. Aspect: Flower and seed capsule are connected. Peduncle: Strong and upright.

*Individual flowers.*—Size: 35–40 mm. Color: Upperside: Red purple 62D with darker centers and in certain instances darker edges. Underside: Red purple 62D. Borne: On 5–7 or more flower stems, each carrying up to 7 flowers. Shape: Violet shape; two small and three large petals; several flowers have additional petals in the center giving the appearance of a semi-double flower. Corolla: Upright flower stems form a compact flower head free above the leaves. Flowering time: In 9–10 weeks after potting, a saleable plant with a full bouquet appears.

*Reproductive organs.*—Stamens: Two anthers composed of four cells. Filaments: Pinkish in color. Styles: Dark pink light stigma.

*Roots.*—White when young and active; brownish when older.

*Disease resistance.*—Good as experienced to date.

I claim:

1. A new and distinct cultivar of African violet plant named Improved Louisiana, as illustrated and described, and particularly characterized by its compact growth habit, strong and upright flower stems, frilled flowers which are light pink accentuated with darker pink spots around the center and in certan instances darker pink at the edges, and by its dark green and indented leaves.

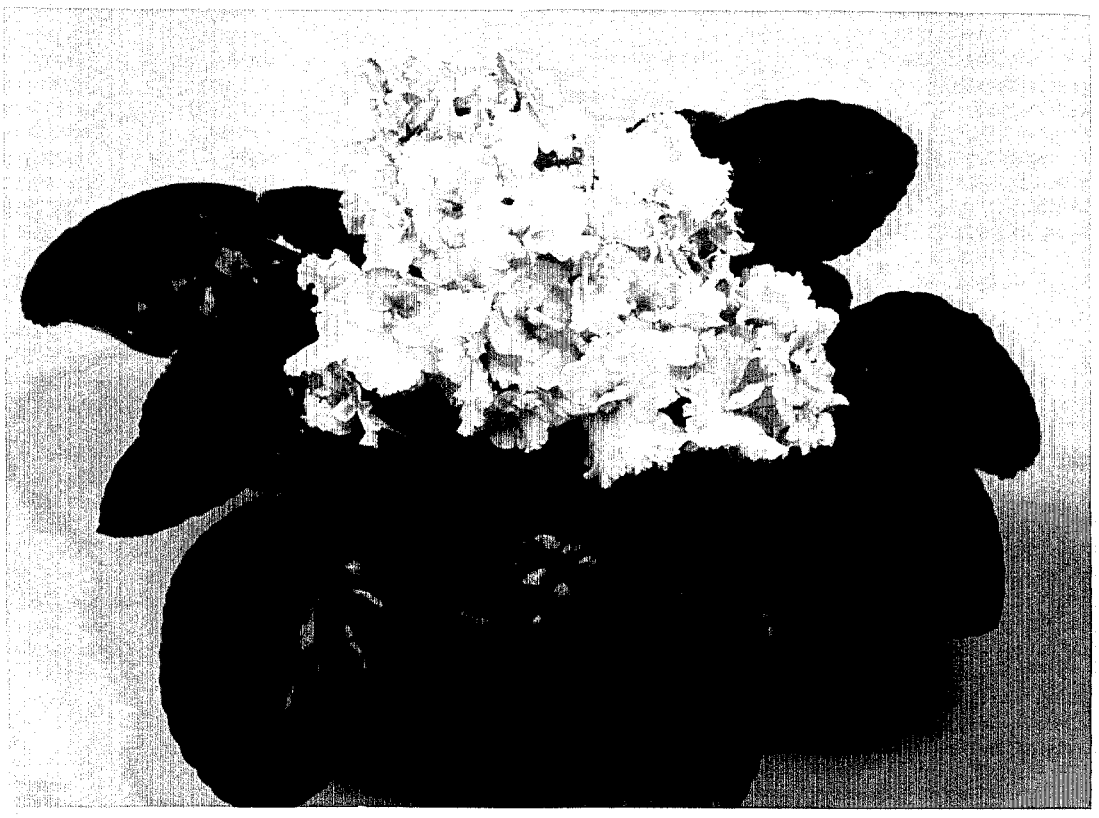

* * * * *